United States Patent [19]

Dotan et al.

[11] Patent Number: 5,216,479
[45] Date of Patent: Jun. 1, 1993

[54] OPTICAL INSPECTION SYSTEM FOR DISTINGUISHING BETWEEN FIRST AND SECOND COMPONENTS IN A LAMINATE

[75] Inventors: Noam Dotan, Givatayim; Abraham Gross, Rehovot, both of Israel

[73] Assignee: Optrotech Ltd., Nes Ziona, Israel

[21] Appl. No.: 735,328

[22] Filed: Jul. 24, 1991

[30] Foreign Application Priority Data

Jul. 27, 1990 [IL] Israel .......................................... 95205

[51] Int. Cl.⁵ ..................... G01N 21/00; G01N 21/45; G01N 21/25
[52] U.S. Cl. ...................................... 356/73; 356/445; 356/446; 356/237; 356/417
[58] Field of Search ............... 356/417, 237, 317, 318, 356/73, 445, 446; 250/458.1, 459.1, 461.1, 461.2

[56] References Cited

U.S. PATENT DOCUMENTS

| | | | |
|---|---|---|---|
| 4,152,723 | 5/1979 | McMahon et al. | 358/106 |
| 4,556,903 | 12/1985 | Blitchington et al. | 358/106 |
| 4,600,951 | 7/1986 | Blitchington et al. | 358/280 |
| 4,601,576 | 7/1986 | Galbraith | 356/237 |
| 4,692,690 | 9/1987 | Hara et al. | 356/237 |
| 4,943,154 | 7/1990 | Oetliker et al. | 356/417 |

Primary Examiner—F. L. Evans
Assistant Examiner—K. P. Hantis
Attorney, Agent, or Firm—Helfgott & Karas

[57] ABSTRACT

An optical inspection system for distinguishing between a laminate formed of a first component having a second component disposed on a first surface thereof, comprising a collection optics including a cylindrical concave elliptical reflecting surface and having a first focal line coplanar with a first surface of the laminate. A light source in fixed spatial relationship with the collection optics directs a first beam of light through an aperture in the elliptical reflecting surface towards the laminate so as to strike the surface along the first focal line and to produce a substantially conical fluorescent emission and so as to be reflected as a substantially conical reflection beam from respective first and second components of the laminate. A filter is disposed near a second focal line of the elliptical reflecting surface for separating the fluorescent emission from the reflection beam. First and second collectors collect the separated fluorescent emission and the separated reflection beam both emanating from limited areas of the laminate, while an analyzing means is coupled to the first and second collectors and responsive to respective collector signals for analyzing the first and second components of the laminate.

18 Claims, 11 Drawing Sheets

OPTICAL INSPECTION SYSTEM FOR DISTINGUISHING BETWEEN FIRST AND SECOND COMPONENTS IN A LAMINATE

FIELD OF THE INVENTION

This invention relates to an optical inspection system for distinguishing between first and second components in a laminate. In particular, it is related to such a system for use with the inspection of printed circuit boards (PCBs).

BACKGROUND OF THE INVENTION

Optical inspection systems for distinguishing between the epoxy substrate and copper tracks of a PCB are well known. Thus, for example, U.S. Pat. No. 4,152,723 (McMahon et al.) describes a method and apparatus for generating a digital image representation of a printed circuit board having a substrate of insulated material and a pattern of metallic conductors disposed on a surface thereof. A beam of light energy scans the surface in a predetermined pattern so as to induce a detectable fluorescence in the surface of the insulating material. The fluorescence is detected and a binary signal is generated to indicate the presence or absence of fluorescence as the beam scans the surface.

Typically, a Helium-Cadmium laser is used which emits a blue beam resulting in a relatively strong yellow fluorescence when the laser beam is incident on the PCB substrate. A filter allows the yellow fluorescence to pass therethrough but blocks the blue laser beam reflected from the copper tracks. The collected fluorescence is detected and analyzed in order to provide an accurate representation of the PCB's surface despite the fact that etched conductive foils often have irregular surfaces.

In fact, since the fluorescent signal is emitted only when the substrate is struck by the laser beam, such a system provides a good indication of the presence or absence of copper track on the insulating substrate but gives no indication relating to the surface quality of the copper track itself. It is therefore known to collect the laser beam reflected from the copper track in addition to the fluorescent emission produced by the insulating substrate, thereby not only to distinguish between the substrate and copper track but, moreover, to analyze surface irregularities within the copper track itself.

Thus, for example, U.S. Pat. No. 4,556,903 (Blitchington et al.) discloses such a system wherein respective fluorescence and reflected beams are produced when a laser beam strikes the substrate and the copper track of a printed circuit board. In the system described by Blitchington et al., both signals are collected, after suitable filtering, so that analysis of the copper track itself may also be undertaken. In particular, such a system permits the uniformity of the copper conductors to be established.

However, in practice, there are many other possible deformities associated with the copper tracks which a practical inspection system must address. PCBs commonly include several layers of conductive track within an insulating substrate, electrical conduction between one or more of the so-called "multilayers" being effected via plated through-holes or "vias" drilled through the PCB. In such a PCB, the major types of defects include:

(a) shorts and surface shorts between conductors;
(b) cuts in conductors;
(c) pin-holes in conductors;
(d) conductor width violation: (comprising local violation, i.e. nick-down or "mouse bites" as well as global width violations);
(e) insulator width violation; and
(f) defects in the conductive tracks which do not penetrate through the complete height of the conductive track down to the laminate, but merely reduce the depth of the conductor (known as "dish-down").

Additionally, there exist three major types of defect related to the plated through-holes, or vias, these being:
(a) hole incompletely drilled;
(b) breakage in hole sleeve; and
(c) hole incorrectly centered relative to a surrounding solder pad.

It is known that systems which rely on the reflection method alone produce many false alarms since it is difficult to detect all of the defects in a PCB owing to the oxidation of the conductive tracks and the poor reflection from very narrow shorts. This problem led to the development of the systems described above which distinguish between the conductive track and the laminate by means of the fluorescence produced by the laminate consequent to its illumination by a specified laser light source.

On the other hand, there are features such as dish-down, wherein the conductive track is not completely eroded but is of reduced thickness, which can only be detected based on the reflection of light therefrom.

Additionally, as was explained above, there currently exists no satisfactory method for inspecting imperfections in the plated through-holes, particularly in combination with the fluorescence and reflection based systems of the type described.

SUMMARY OF THE INVENTION

It is an object of the invention to provide a system for PCB inspection in which the drawbacks of hitherto proposed systems are significantly reduced or eliminated.

According to a broad aspect of the invention there is provided an optical inspection system for distinguishing between a laminate formed of a first component having a second component disposed on a first surface thereof, the system comprising:

a collection optics including a cylindrical concave elliptical reflecting surface and having a first focal line coplanar with the first surface of the laminate, a light source in fixed spatial relationship with the collection optics for directing a first beam of light through an aperture therethrough towards the laminate so as to strike the first surface along the first focal line and to produce a substantially conical fluorescent emission having a first apex angle from a first area of the first component and so as to be reflected as a substantially conical reflection beam having a second apex angle from a second area of the second component, a first filter disposed near a second focal line of the elliptical reflecting surface for intercepting the fluorescent emission and the reflection beam and for separating the fluorescent emission from the reflection beam, a first collector for collecting the separated fluorescent emission emanating from a limited area of said first area and producing a respective first collector signal, a second collector for collecting the separated reflection beam emanating from a limited area of said second area and producing a respective second collector signal, and analyzing means coupled to the first and second collectors and responsive to the respective first and second collector signals for analyzing the first and second components of the laminate.

Preferably, respective pairs of limit stops are provided for limiting the respective areas within the first and second areas over which the fluorescent emission and separated reflection beam are collected. Additionally, a third pair of limit stops is provided so as to limit collection of the conical reflection beam to within a predetermined fraction of the second apex angle.

In accordance with a preferred embodiment of the invention, a third collector is provided disposed towards a second surface of the laminate opposite the first surface and remote from the light source so as to collect a beam passing through the laminate and producing a respective collector signal in response thereto. The analyzing means are responsively coupled to the third collector for analyzing defects in a hole in the laminate permitting the laser beam to pass therethrough.

The second and third collectors include optical light guides formed of a fluorescent material and shielded by a filter which permits the laser beam to pass therethrough but blocks any fluorescence induced within the material of the light guide. The light passing through the holes in the laminate pass through the filters shielding the respective optical light guides so as to induce fluorescence therein, which fluorescence propagates along the light guide owing to total internal reflection and is reflected at an end thereof so as to be collected at an opposite end thereof.

When such a system is used for analyzing defects in the plated through-holes or vias, differences in the transmittance of the light source through the substrate and the plated through-hole itself are exploited. Furthermore, any imperfections in the conductive through-plating yields fluorescence from the thus exposed substrate which may likewise be detected.

BRIEF DESCRIPTION OF THE DRAWINGS

For a clearer understanding of the invention and to see how the same may be carried out in practice, a preferred embodiment will now be described, by way of nonlimiting example only, and with reference to the accompanying drawings, in which:

FIG. 2a is a cross-sectional view through a printed circuit board showing light scattering due to surface deformities in the conductive track;

FIG. 2b is a graphical representation showing the distribution of fluorescent emission as a function of radial distance from the point of contact of the laser beam in FIG. 2a;

DETAILED DESCRIPTION OF A PREFERRED EMBODIMENT

Figure 1:
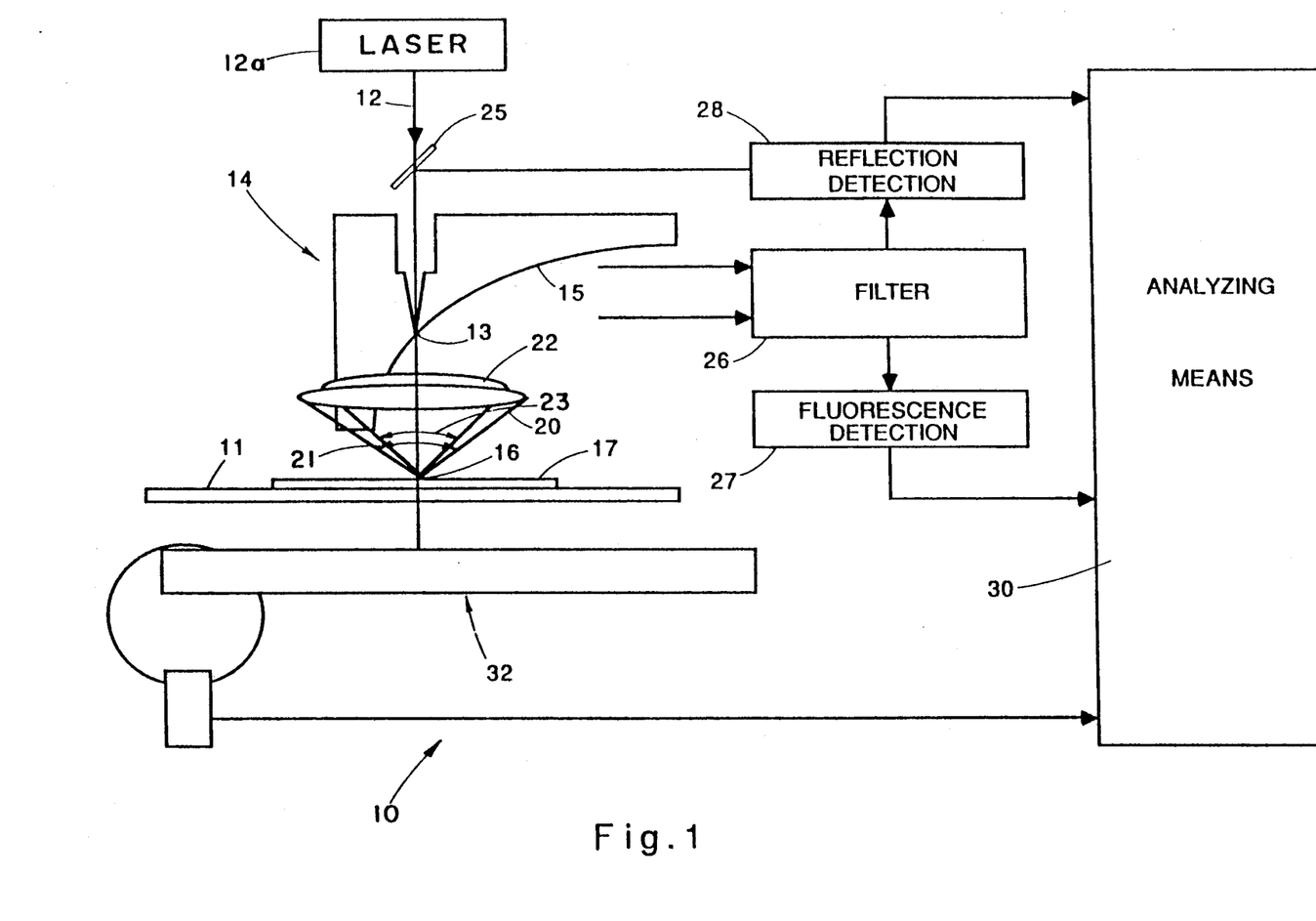
FIG. 1 is a block diagram showing functionally an automatic PCB inspection machine in accordance with the present invention.

FIG. 1 is a block diagram showing functionally a system depicted generally as 10 for analyzing defects in a printed circuit board 11. A Helium-Cadmium laser 12a produces a laser beam 12 having a characteristic blue color which is directed through an aperture 13 in a collection optics 14 including a cylindrical concave elliptical reflecting surface 15 having a first focal line 16 coplanar with an upper surface 17 of the PCB 11 (and constituting a first surface of the laminate).

On striking the first surface 17, there is induced in the laminate a substantially conical fluorescent emission 20 having a first apex angle 21 and there is reflected from a conductive track on the first surface 17 a substantially conical reflection beam 22 having a second apex angle 23. The PCB laminate is formed of a first component, whilst the conductive track is formed of a second component.

In addition to the reflection beam 22, some of the laser beam 12 striking the first surface 17 of the PCB 11 will be reflected back through the aperture 13 and this specular reflection must also be accounted for. This is achieved by means of a beam splitter 25 which allows most of the laser beam 12 to pass therethrough but reflects most of the reflected beam 22 passing through the aperture 13. The fluorescent emission is separated from the reflection beam by a filter 26 whereupon all of the fluorescent emission and all of the reflected beam, including the specular reflection accounted for by the beam splitter 25, are collected by respective first and second collectors 27 and 28 whose respective outputs are analyzed by an analyzing means depicted generally at 30.

In the event that the laser beam 12 passing through the aperture 13 meets a plated through-hole (not shown) in the PCB 11, at least some of the laser beam 12 will pass therethrough so as to be collected by a third collector depicted generally as 32 whose output is likewise analyzed by the analyzing means 30.

In such a system, the analyzing means 30 permits analysis of defects in the PCB 11 according to the relative quantities of reflected light and fluorescent emission produced as a result of laser beam 12 striking the PCB 11. The manner in which such analysis is performed is not itself a feature of the present invention, such analysis being known per se in the art and being described, for example, in above-mentioned U.S. Pat. No. 4,556,903. However, in the present system, the collection optics 14 is mutual to the collection of the fluorescent emission and the reflection beam and, in particular, permits collection of the fluorescent emission and the reflection beam over very large angles. The need to collect over wide angles is different with respect to the fluorescent emission and the reflection beam. Specifically, collecting the fluorescent emission over a wide solid angle helps to overcome the problem of very low light level and obviates the need for high signal-to-noise ratio resulting from the relative low intensity of the fluorescent emission compared with the laser beam 12.

In contrast to this, collection of the reflection beam over a wide solid angle is desirable so as maximally to suppress top surface mottling effects in the conductive track. The optical collection system allows for the separation of the fluorescent emission from the reflected laser beam and, as will become clear below with paricular reference to FIG. 6 of the drawings, permits the area of the surface 17 from which the fluorescent emission 20 and the reflected beam 22 are collected to be respectively adjusted. Additionally, means are provided for limiting the angle of the collected reflection beam so as thereby to determine surface irregularities in the conductive track.

Figures 2A, 2B:
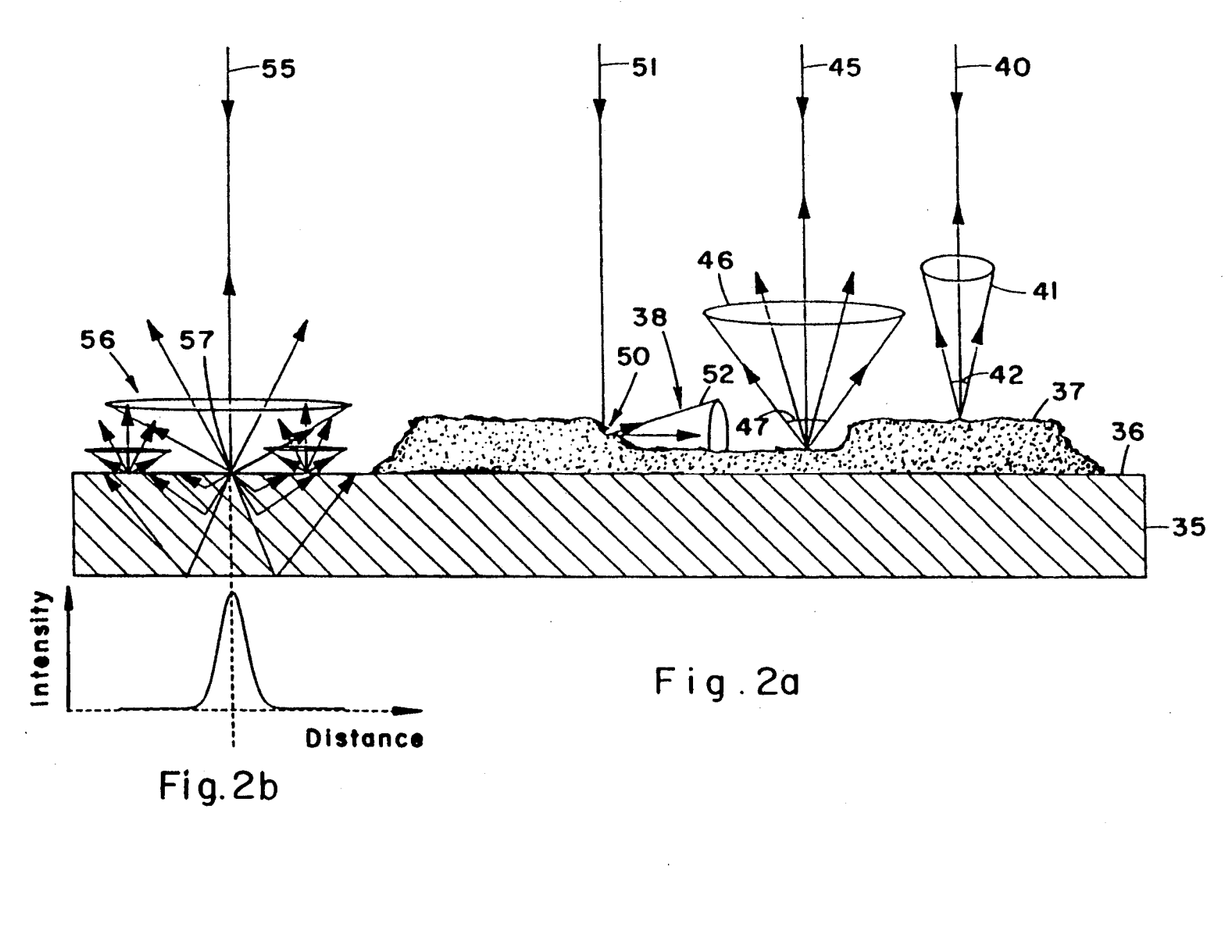

Referring now to FIG. 2 of the drawings, the need to adjust the angle over which the reflected beam 22 is collected and the need to collect the fluorescent emission 20 over as wide an angle as possible will become apparent. FIG. 2 shows a PCB comprising an insulating laminate 35 having on a first surface 36 thereof a conductive track 37. The height of the conductive track 37 varies owing, in part, to surface irregularities and, in particular, where during etching a local area has been eroded resulting in so-called "dish-down" 38.

The laser beam 12 is in fixed spatial relationship with the collection optics 14 and performs scanning of the printed circuit board, so that at any instant of time light will either be reflected from the conductive track 37 or, alternatively, will induce fluorescence within the insulating substrate 35.

The angle over which the laser beam is reflected depends on the surface regularity of the conductive track 37. Specifically, the more uniform is the surface of the conductive track 37, the narrower is the angle over which the laser beam is reflected. The reflected beam scatters much more than the numerical aperture of the incoming laser beam, owing to the mottling effect of the top surface of the conductive track 37. The angle of the reflected cone depends on the nature of the conductor surface exposed to the laser beam which, in turn, depends on the conductor material and any treatment effected thereto. Thus, for example, a chemical and pumice cleaning process will leave the metal in a diffusing state, whilst brushing and scrubbing the conductor surface will leave it shiny and highly specular. In order to cover all eventualities, there is an obvious need for wide angle collection.

These effects are shown pictorially in FIG. 2a where, for example, an incoming laser beam 40 is reflected from a polished surface of the conductive track 37 resulting in a conical reflection beam 41 having a narrow apex angle 42. In contrast to this, the area 38 of the conductive track 37 is subject to "dish-down" deformation owing to excessive etching resulting in the erosion of a greater volume of conductive material and also producing a rougher surface. Also surface cleaning and polishing is less effective on the exposed surface of the "dish down" area 38. Consequently, a laser beam 45 striking the area 38 is reflected as a conical reflection beam 46 having an apex angle 47 significantly greater than the apex angle 42 associated with the reflection beam 41.

It will also be noted that a sidewall 50 of the "dish-down" area 38 is chamfered such that an incoming laser beam 51 is reflected therefrom as a conical reflection beam 52 in a direction substantially normal to the direction of propagation of the incoming laser beam 51. In order to detect "dish-down", collection of the conical reflection beam 52 must be avoided. Likewise, only part of the fluorescent emission 46 must be collected, whilst all of the reflection beam 41 must be collected. In order to achieve these requirements, the collecting optics must be adapted to collect over a wide, but controllable, angle.

Also shown is a laser beam 55 which strikes an area of the substrate 35 uncovered by a conductive track and which therefore produces a fluorescent emission, shown generally as 56. In fact, the laser beam 55 penetrates the laminate 35 at a single point 57 (being the apex of the conical fluorescent emission 56) but, owing to internal scattering, light emerges from the laminate over a much wider area. In order to reduce the collected light from the laminate 35, the field of view is restricted in one dimension to a narrow strip.

Also shown in FIG. 2b is a graphical representation showing the distribution of fluorescent emission as a function of radial distance from the point of contact 57 of the laser beam 55. It will be seen that distribution is maximum at the point of contact 57 and trails off as the radial distance increases.

Figure 3A:
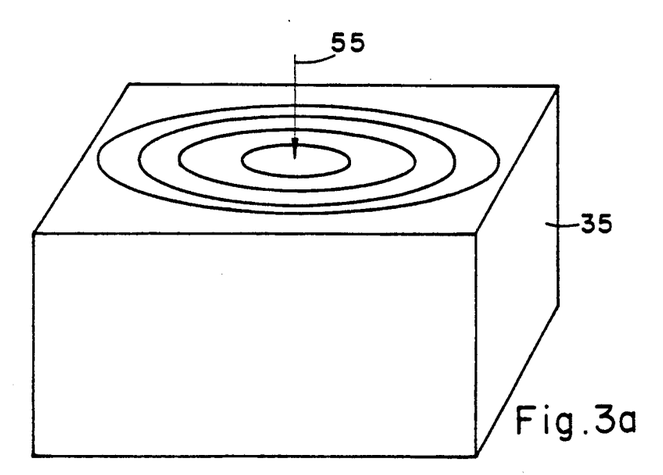
FIG. 3a is a cross-sectional view through a printed circuit board showing the correlation between surface reflection and field of view.
Figure 3B:
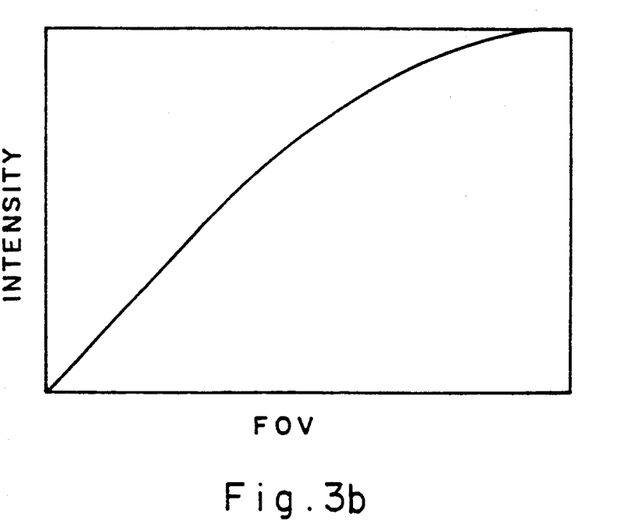
FIG. 3b shows a graph illustrating the increase in intensity with the field of view.

FIG. 3a shows pictorially the ripple effect of the fluorescent haloes created as a result of internal reflection within the substrate 35 as well as a graphical representation of the intensity of the reflection beam as a function of the field of view. In this connection, it will be understood that some of the laser beam 55 will be reflected even from the substrate 35 albeit obviously not to the same degree as that which is reflected from the conductive track. It will thus be seen from FIG. 3b that the intensity increases with the field of view, such that when the field of view exceeds a certain threshold, the intensity of the reflection beam reaches a maximum.

Figure 4A:
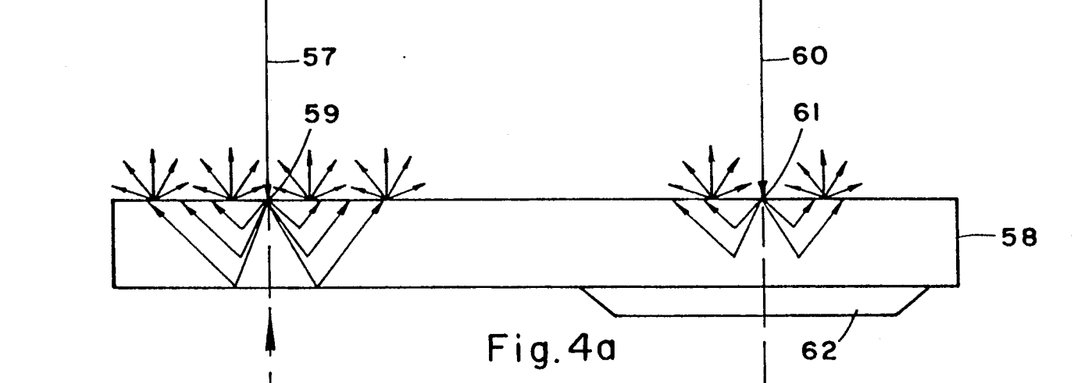
FIG. 4a is a cross-sectional view through a printed circuit board showing the correlation between surface fluorescent emission and field of view.

FIG. 4 shows graphically the spatial distribution of the fluorescent emission as a function of the field of view (FOV) consequent to a laser beam 57 striking a substrate 58 at a first point 59 whereat the laser beam 57 comes into contact only with the insulating substrate 58. Also shown is a laser beam 60 striking the substrate 58 at a second point 61, there being located underneath the substrate 58 a conductive copper track 62.

Figure 4B:
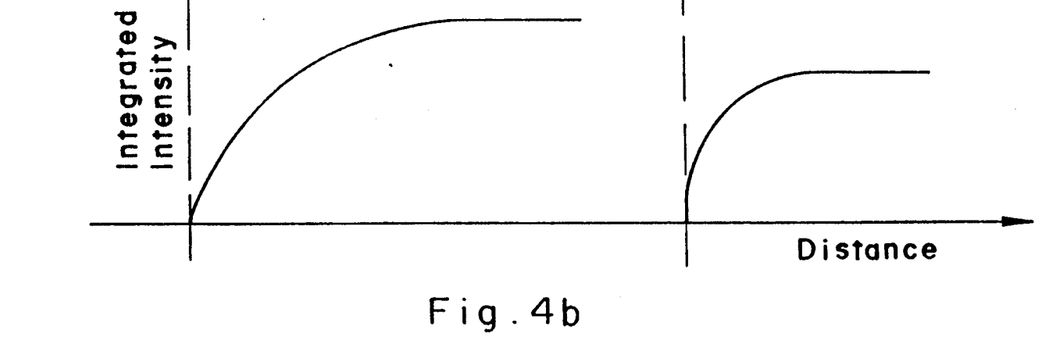
FIG. 4b shows a graph illustrating the variation of fluorescent emission intensity with FOV.

The variation of fluorescent emission intensity with FOV (FIG. 4b) is seen to depend on the thickness of the substrate 58 and is influenced by the presence of the conductive track 62 on the underside of substrate 58. In both cases, the fluorescent emission has a Lambertian angular distribution shape and has a halo, or ripple, effect similar to that shown in FIG. 3b relating to the reflection beam. In order to eliminate variation of fluorescent light level (known as the dynamic range of the fluorescent light level), the field of view is restricted in one dimension to a narrow strip from both sides of the point of contact by the laser beam on the PCB, in a manner similar to that employed to reduce the field of view of the reflection beam.

Figure 5:
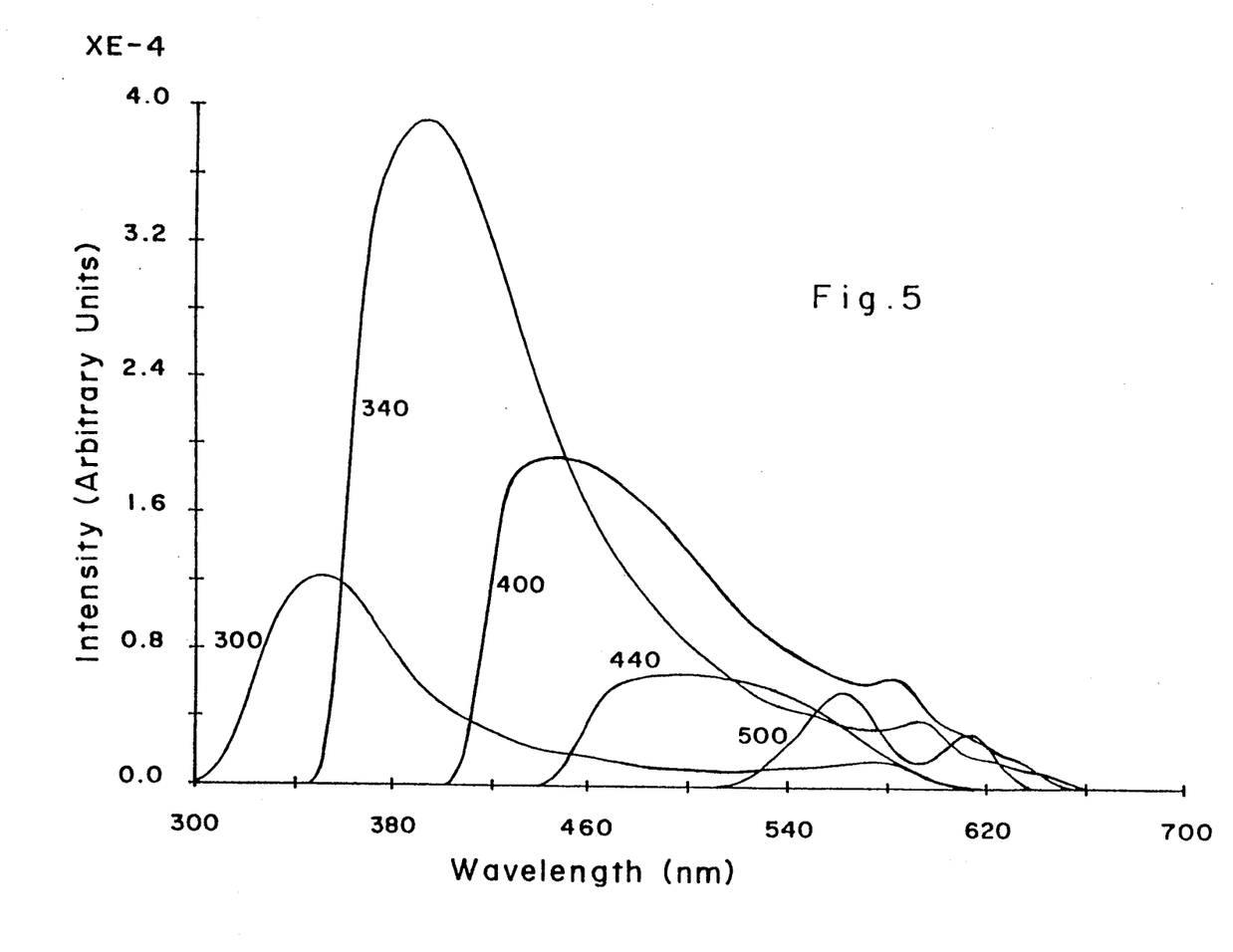
FIG. 5 is a graphical representation of a fluorescent emission spectrum of an FR-4 substrate when excited by various wavelength light sources.

FIG. 5 is a graphical representation showing typical emission spectra of a FR-4 laminate excited by a plurality of light sources having wavelengths of 300, 340, 400, 440 and 500 nm. In order to collect the fluorescent emission and distinguish it from the laser reflection beam, an optical filter must be used. This filter must be optimized to match the excitation wavelength and the wavelength of the corresponding fluorescent emission. Also, bearing in mind that the power of the laser beam exceeds that of the fluorescent emission by a factor of $10^6$, the filter must allow no more than one part of the laser light to pass for each $10^8$ parts of the fluorescent emission, in order that the error associated with the separated fluorescent emission will be acceptable.

Much of what has been stated above relates generally to the nature of the fluorescent emission and the reflected beam and is well known in the art. There will now be described with particular reference to FIG. 6 of the drawings an optical arrangement which permits the desiderata described above to be realized in practice. To the extent that some of the elements shown in FIG. 6 have already been described above with reference to FIG. 1, identical reference numerals will be employed.

Figure 6:
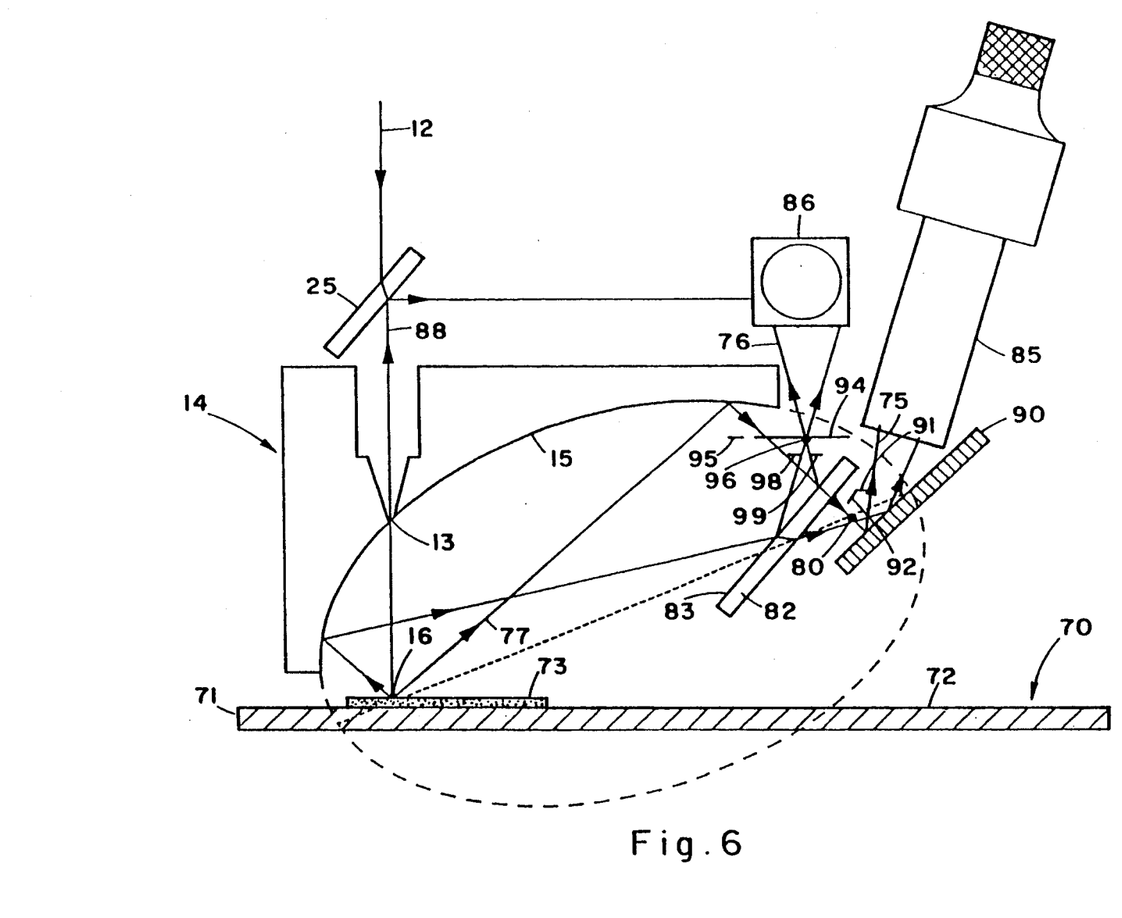
FIG. 6 is a pictorial representation showing a cross-sectional view of a collection optics for use in the system shown in FIG. 1.

Thus, shown in FIG. 6 is a printed circuit board designated generally as 70 comprising an insulating laminate 71 having on a first surface 72 thereof a conductive copper track 73.

The laser beam 12 is directed via a beam splitter 25 through the aperture 13 in the collection optics 14 on to upper surface 72 (constituting a first surface) of the PCB 70. The laser source (not shown), the beam splitter 25 and the collection optics 14 are maintained in a fixed spatial relationship with respect to each other, the PCB 70 being scanned across its first surface 72 in a manner well known in the art. For example, scanning may be effected in a lateral direction using a rotary polygonal mirror, scanning being effected in the perpendicular, longitudinal direction by moving the printed circuit board 70.

The first focal line 16 of the cylindrical concave elliptical reflecting surface 15 of the collection optics 14 is coplanar with the first surface 72 of the printed circuit board 70 so that, in effect, the laser beam 12 strikes the printed circuit board 70 along the first focal line 16. Since the insulating laminate 71 reflects some of the laser beam 12 as well inducing fluorescence, the incoming laser beam 12 will produce a fluorescent emission 75 and a reflection beam 76 simultaneously and these must be separated in order to permit analysis of the printed circuit board 70.

Separation of the fluorescent emission 75 from the reflection beam 76 is no easy matter bearing in mind that a powerful laser source is employed which has a tendency to swamp the relatively weak fluorescent emission 75 induced in the insulating laminate 71. Typically, the reflection beam 76 has a power in the order of $10^6$ times that of the fluorescent emission 75 and, for this reason, correction of the fluorescent emission 75 over as wide an angle as possible is required in order to maximize the power of the collected fluorescent emission.

In FIG. 6, the reflection of the laser beam 12 from the first surface 72 of the printed circuit board 70 is shown generally as a conical beam 77 having an apex angle of the order of 100°, which strikes the elliptical reflecting surface 15 so as to be reflected therefrom towards a second focal line 80 thereof. It will, of course, be understood that a geometrical property of a concave, elliptical reflecting surface is that a source of light emanating from one focus thereof will be reflected towards the other focus. This fact is exploited in the collection optics 14 in order to guarantee substantially total collection of the beam 77 comprising the fluorescent emission 75 and the reflection beam 76 components.

A filter 82 (constituting a first filter) is disposed near the second focal line 80 of the elliptical reflecting surface 15 for intercepting the beam 77 (reflected from the elliptical reflecting surface 15) and to separate the two components by allowing the fluorescent emission 75 to pass therethrough whilst reflecting the reflection beam 76 from a front surface 83 thereof. The separated fluorescent emission 75 is collected by a first collector 85, whilst the separated reflection beam 76 is collected by a second collector 86.

A component 88 of the laser beam 12 is reflected upwards from the first surface 72 of the printed circuit board 70 through the aperture 13 so as to strike the beam splitter 25 and to be reflected therefrom towards the second collector 86. Thus, the second collector 86 is responsive to both components 76 and 88 of the reflection beam for producing accurate results.

The manner in which the fluorescent beam 75 is collected is as follows. A planar mirror 90 (constituting a first planar reflecting surface) is disposed towards a rear surface of the filter 82 behind the second focal line 80 for reflecting the fluorescent emission 75 towards the first collector 85. Disposed near the second focal line 80 and thus between the rear surface of the filter 82 and the mirror 90 is a first pair of limit stops 91 and 92 which, in the figure, are shown as being contiguous although they need not be. The limit stops 91 and 92 are adjustable so as partially to intercept the reflected fluorescent emission 75 and thereby to limit the area over which fluorescent emission induced within the insulating laminate 71 is collected.

Likewise, a second pair of adjustable limit stops 94 and 95 (constituting a second pair of limit stops) disposed collinear with a reflection 96 of the second focal line 80 through the filter 82, so as partially to intercept the separated reflection beam (reflected from the front surface 83 of the filter 82) and thereby to limit the area from which the laser beam 12 reflected from the front surface 72 of the PCB 70 is collected by the second collector 86. It will be understood that, in the preferred embodiment, the second pair of limit stops 94 and 95 are located collinear with the reflection of the second focal line 80 through the filter 82 but optically exactly the same results ensue if the second pair of limit stops 94 and 95 are disposed collinear with the second focal line 80 itself.

Finally, a third pair of adjustable limit stops 98 and 99 is disposed between the front surface 83 of the filter 82 and the reflection 96 of the second focal line 80, so as partially to intercept the separated reflection beam 76 and thereby to limit the collection angle within the conical reflection 77 over which the reflection beam 76 is collected.

Thus, the first and second pairs of limit stops 91,92 and 94,95, respectively, limit the respective fields of view of the fluorescent and reflection beams 75 and 76, i.e. the area on the first surface 72 of the printed circuit board 70 over which the fluorescent emission 75 and the reflection beam 76 are collected. By reducing the field of view of the fluorescent emission 75, variation of the fluorescent emission, i.e. the dynamic range of the fluorescent emission, may be substantially eliminated. In effect, even though, as was explained above, the laser beam is reflected and fluorescent emission is induced over a greater area than a single track width, the first and second pairs of limit stops permit the reflected beam and the fluorescent emission collected to be restricted to those emanating only from the point of contact on the PCB 70 by the laser beam 12. Likewise the third pair of limit stops, 98,99 functions as an angle discriminatory whose width determines the angle over which the reflected beam 76 is collected.

Figure 7:
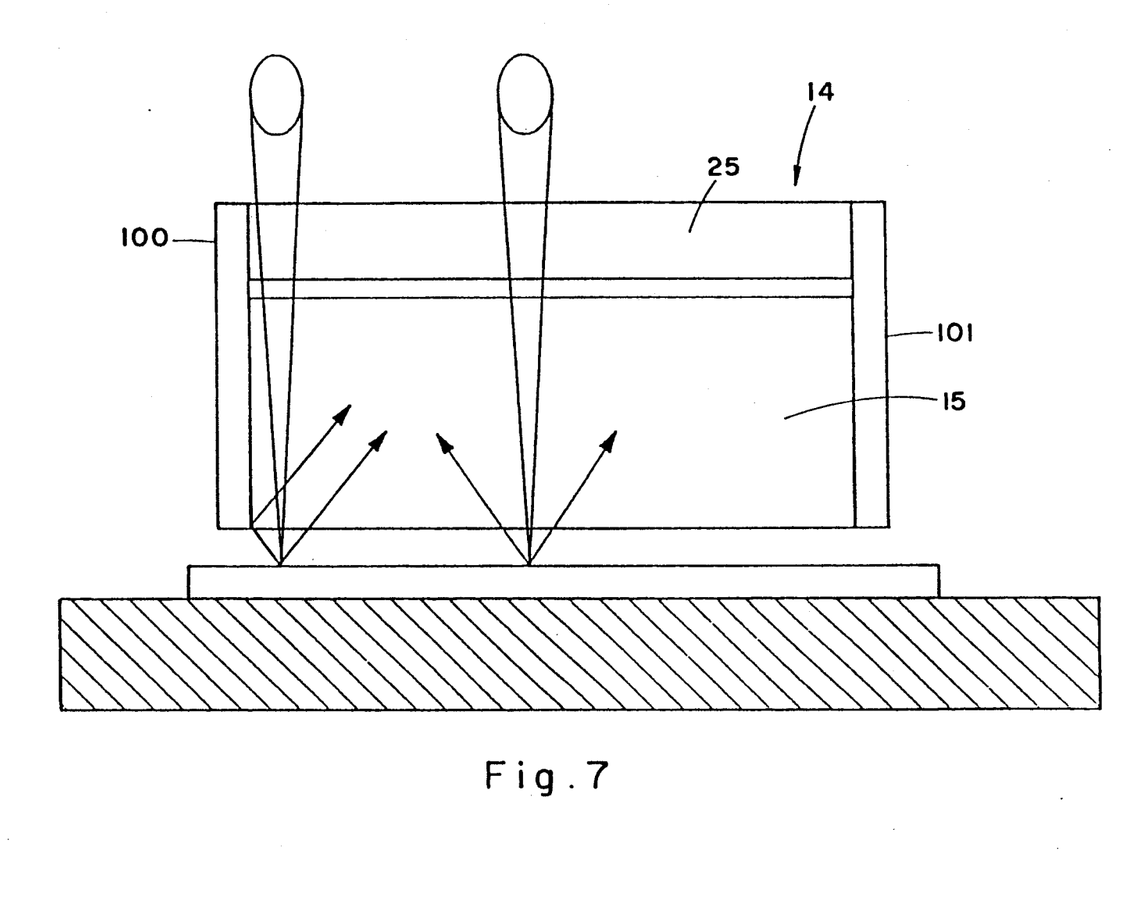
FIG. 7 is a side view of the collection optics shown in FIG. 6.

Referring to FIG. 7 there is shown a side elevation of the arrangement shown in FIG. 6 (not drawn to scale) showing a pair of planar reflecting surfaces 101 disposed at opposite sides of the elliptical reflecting surface 15 so as to form an image thereof and thereby increase the effective area of the collection optics 14.

Figure 8A:
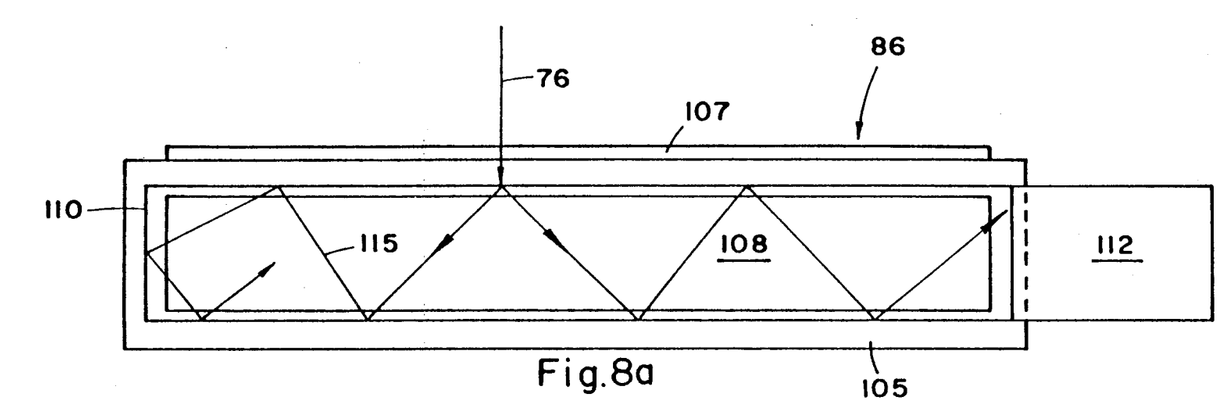
FIGS. 8a and 8b show a collector and an associated detector for collecting a reflection beam in the system shown in FIG. 1.

Referring now to FIG. 8a there is shown in greater detail the second collector 86 for collecting the two components of the reflection beam 76 and 88. The second collector 86 includes an optical light guide 105 formed of a fluorescent acryl and shielded by respective blue dichroic filters 107 and 108 on adjacent faces thereof. At a first end of the optical light guide 105 is disposed a planar reflecting surface 110 whilst at an opposite end is disposed a photomultiplier tube 112 (constituting a detector).

The reflection beam 76 is directed to the optical light guide 105 through a first one of the blue dichroic filters 107 whilst the component 88 (see FIG. 6) is directed to a second one of the blue dichroic filters 108. Upon passing through the blue dichroic filters 107 and 108, both components 76 and 88 of the reflection beam induce fluorescence within the optical light guide 105. The fluorescence is induced within corresponding walls 113 and 114 of the optical light guide 105 and is totally internally reflected within the optical light guide 105 as a beam 115. The internally reflected beam 115 propagates through the optical light guide 105 and is reflected by the reflecting surface 110 back towards the photomultiplier tube 112, so that substantially all of the light entering the optical light guide 105 and internally reflected therein is collected thereby.

Figure 8B:
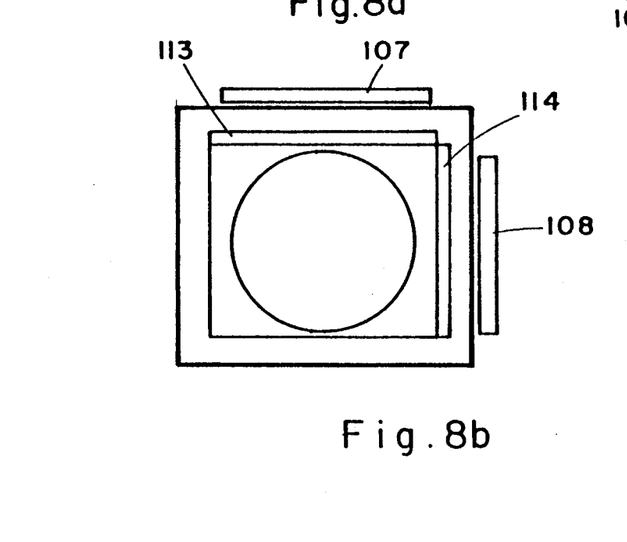

The blue dichroic filters 107 and 108 also shown in FIG. 8b prevent passage therethrough of the fluorescent emission beam 115 induced within the optical light guide 105 and thus blocks the beam 115 from reaching the first collector 85 which detects the fluorescent emission 75 (see FIG. 6).

As has been explained above with particular reference to FIG. 6 of the drawings, the angle over which the reflected beam 76 is collected may be varied by means of the third pair of limit stops 98 and 99. In fact, the limit stops 98 and 99 only affect the collection angle within the plane of FIG. 6 and not in a plane mutually perpendicular thereto. The blue dichroic filters 107 and 108 have the property that they only allow light to pass therethrough whose angle of incidence is below a predetermined threshold. By this means, the collection angle of the reflection beam 76 (FIG. 6) in the plane perpendicular to FIG. 6 may also be controlled.

Figure 9:
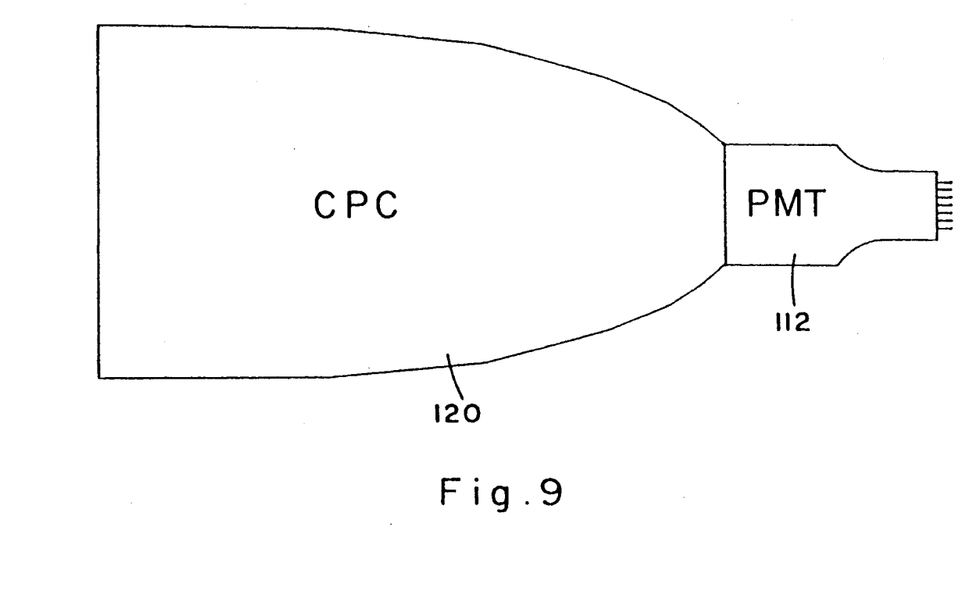
FIG. 9 is a pictorial representation of a compound parabolic collector and photomultiplier tube for detecting a fluorescent emission in the system shown in FIG. 1.

FIG. 9 shows a detail of the photomultiplier tube 112 shown in FIG. 8 which is coupled to a compound parabolic collector 120 which allows for light collected along the length of the optical light guide 105 to be collected by a photomultiplier tube 112 having a relatively small area detector.

Figure 10:
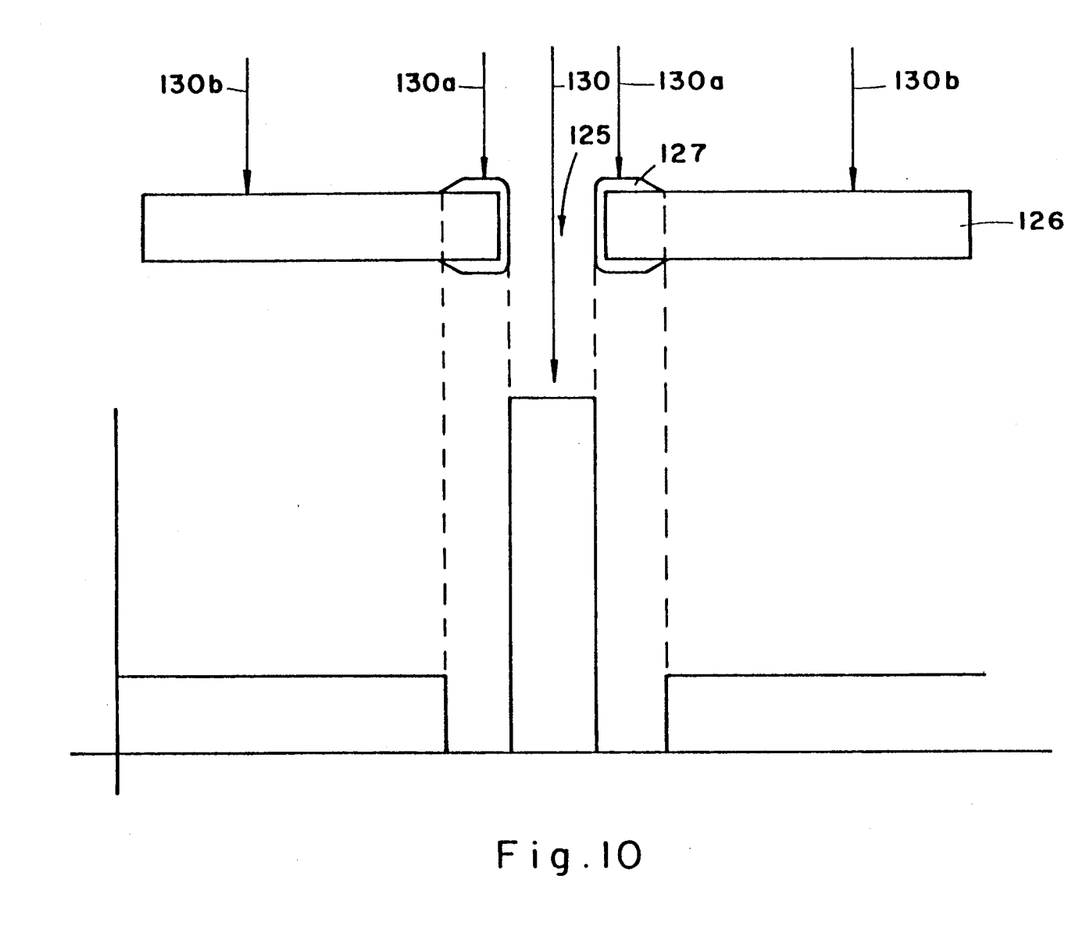
FIG. 10 is a schematic representation showing a measured light level at the bottom of a PCB when illuminated at a top surface with a laser scanner.

Referring now to FIG. 10 there is shown a detail of a hole 125 formed in a PCB laminate 126 and being plated with conductive material 127, such as copper. The laser beam 130 passes directly through the hole 125 when illuminated from above by a telecentric laser scanner. It is evident that the highest light level received will be in the case that the laser beam 130 passes freely through the hole 125. Also shown is the case that the laser beam, shown for the sake of distinction as 130a, strikes the copper plating 127. In this case, the laser beam 130a is reflected from the copper plating 127 and therefore does not penetrate the PCB laminate 126. In a third situation, the laser beam shown as 130b strikes the PCB laminate 126 and, owing to partial absorption and scattering thereby, emerges therefrom with reduced intensity.

Figure 11:
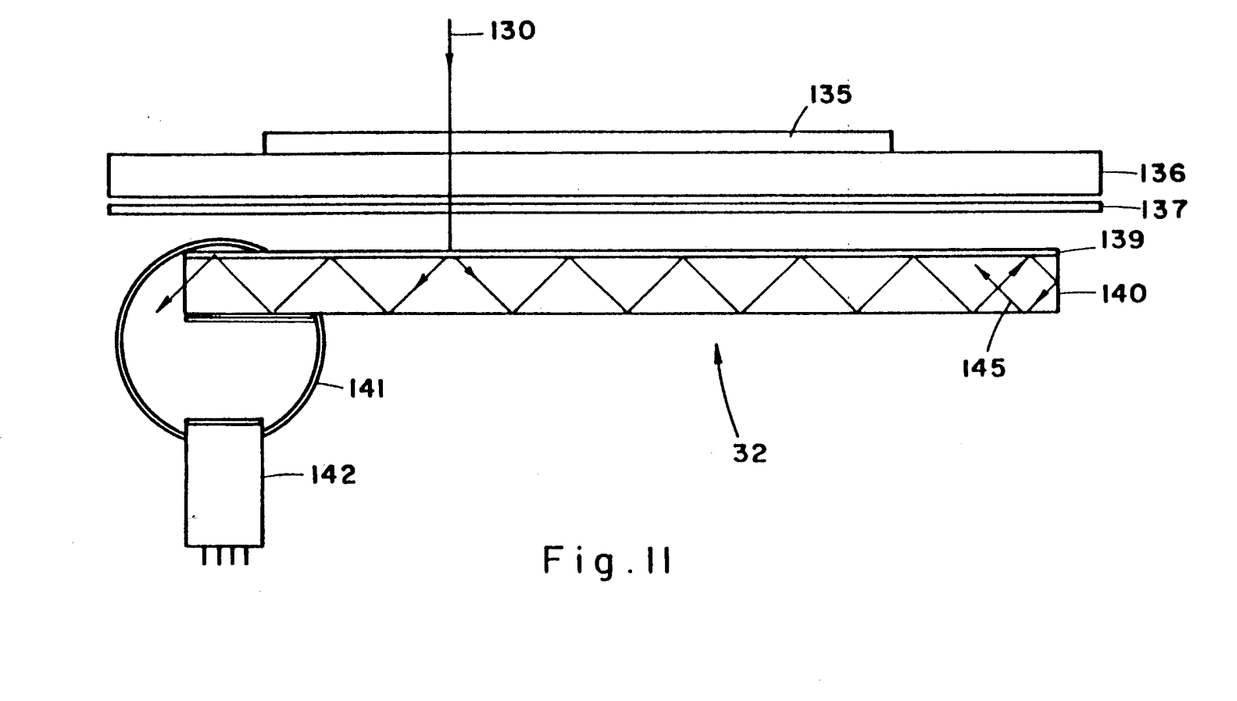
FIG. 11 is a pictorial representation of a hole detection system for use in the system shown in FIG. 1.

FIG. 11 shows in greater detail the third collector 32 shown functionally in FIG. 1 of the drawings. Thus, there is shown a printed circuit board (PCB) 135 mounted on a semi-transparent glass table 136 underneath of which is disposed a blue filter 137. The blue laser beam 130 passes through the PCB 135 with an intensity depending upon the presence or absence of a hole as explained above with reference to FIG. 10 of the drawings and is transmitted by the blue filter 137. The beam emerging from the blue filter 137 is passed to an optical light guide 139 formed of a fluorescent acryl material having at a first end thereof a planar reflecting surface 140 and at a second end thereof opposite the first end an integrating cylinder 141 coupled to a photomultiplier tube 142.

The operation of the optical light guide 139 is substantially identical to that of the optical light guide 105 in the second collector 86 described in detail above with reference to FIG. 8 of the drawings. Thus, the laser beam passing through the blue filter 137 induces fluorescence within the optical light guide 139 which is totally internally reflected therein as a beam 145 which, on striking the reflecting surface 140, propagates back through the optical light guide 139 towards the integrating cylinder 141. Thus, light emerging from the optical light guide 139 is collected by the integrating cylinder 141 and directed to the photomultiplier tube 142. The blue filter 137 prevents any fluorescence induced within the optical light guide 139 from passing back therethrough towards the printed circuit board 136 and hence reaching the first collector 85 which detects the fluorescent emission 75.

It will be apparent that if the laser beam strikes a sidewall of a plated through-hole in the printed circuit board 135, the intensity of the light reaching the optical light guide 139 will vary according to the surface quality of the plated through-hole. Thus, specifically, if the light strikes polished metal it will be substantially reflected as explained above whilst, if owing to a manufacturing flaw, the insulating substrate of the printed circuit board 135 is exposed, correspondingly more light will be transmitted therethrough.

The light emerging from the optical light guide 139 and directed by the integrating cylinder 141 to the photomultiplier tube 142 thus permits analysis of any plated through-holes scanned by the laser beam 130.

Thus, in accordance with the invention, there is provided an inspection system particularly suitable for analyzing defects in printed circuit boards, having a reflection and fluorescent channel both of which are independently controlled so as to vary their respective fields of view. Additionally, the collection angle associated with the reflection beam is also adjustable and an additional channel is provided for the inspection of plated through-holes.

It will be appreciated that, whilst the preferred embodiment has been described with particular reference to a conductive track disposed on an insulating laminate, such that an incoming laser beam is reflected by the conductive track and induces fluorescence in the laminate, other configurations are possible. In particular, it is known to dispose a photoresist on a copper-plated laminate, such that an incoming laser beam is again reflected by the copper but induces fluorescence in the photoresist. Such a configuration also lends itself to analysis by the system according to the invention: the roles of the first and second components being effectively reversed.

We claim:

1. An optical inspection system for distinguishing between first and second components of a first surface of a laminate having said second component disposed on the first component, the system comprising:
    a collection optics including a cylindrical concave elliptical reflecting surface and having a first focal line coplanar with the first surface of the laminate,
    a light source in fixed spatial relationship with the collection optics for directing a first beam of light through an aperture in the collection optics towards the laminate so as to strike the first surface along the first focal line and to produce from a first area of the first component a substantially conical fluorescent emission having a first apex angle and so as to be reflected by a second area of the second component as a substantially conical reflection beam having a second apex angle,
    a first filter disposed near a second focal line of the elliptical reflecting surface for intercepting the fluorescent emission and the reflection beam and for separating the fluorescent emission from the reflection beam,
    a first collector for collecting the separated fluorescent emission emanating from a limited area of said first area and producing a respective first collector signal,
    a first pair of limit stops disposed near the second focal line for partially intercepting the reflected fluorescent emission so as thereby to limit the area within said first area from which fluorescent emission is collected by the first collector,
    a second collector for collecting the separated reflection beam emanating from a limited area of said second area and producing a respective second collector signal, and
    analyzing means coupled to the first and second collectors and responsive to the respective first and second collector signals for analyzing the first and second components of the laminate.

2. The system according to claim 1, wherein the first filter transmits the fluorescent emission therethrough and reflects the reflection beam from a front surface thereof to be focused at an image of the second focal line imaged by the first filter.

3. The system according to claim 2, further including:
    a first planar reflecting surface disposed towards a rear surface of the first filter behind the second focal line of the elliptical reflecting surface, for reflecting the fluorescent emission transmitted by the first filter towards the first collector.

4. The system according to claim 1, further including a second pair of limit stops collinear with a reflection of the second focal line for partially intercepting the separated reflection beam so as thereby to limit the area within the second area from which the separated reflection beam is collected by the second collector.

5. The system according to claim 2, further including a third pair of limit stops disposed between the first filter and a reflection of the second focal line therethrough for partially intercepting the conical reflection beam after it has been separated from the fluorescent emission by the first filter so as thereby to limit collection of the conical reflection beam to within a predetermined fraction of the second apex angle.

6. The system according to claim 4, further including a third pair of limit stops disposed between the first filter and a reflection of the second focal line therethrough for partially intercepting the separated reflection beam after it has been separated from the fluorescent emission by the first filter so as thereby to limit collection of the conical reflection beam to within a predetermined fraction of the second apex angle.

7. The system according to claim 1, wherein the first pair of limit stops is variable.

8. The system according to claim 4, wherein the second pair of limit stops is variable.

9. The system according to claim 5, wherein the third pair of limit stops is variable.

10. The system according to claim 1, wherein the second collector includes:
    a beam splitter intermediate the light source and the elliptical reflecting surface for transmitting the first beam therethrough while reflecting substantially all the reflection beam emerging from the aperture in the elliptical reflecting surface,
    an optical light guide formed of a fluorescent material and being shielded by a pair of second filters on adjacent faces thereof, for preventing passage therethrough of any fluorescence induced within said fluorescent material,
    a second planar reflecting surface at a first end of the optical light guide for reflecting light directed thereto back through the optical light guide as a second beam, and
    a detector at a second end of the optical light guide remote from said first end thereof and responsive to said second beam for producing the second collector signal;
    whereby the reflection beam emerging from said aperture is directed as a first component beam through a first one of said second filters towards a first one of said faces and the separated reflection beam is directed as a second component beam through a second one of said second filters towards a second one of said faces, said first and second component beams passing through the optical light guide and inducing fluorescence in the fluorescent material thereof which fluorescence is internally reflected therein so as to be directed towards the detector while being blocked by the second filters so as to prevent it from escaping from the optical light guide.

11. The system according to claim 10, wherein the detector includes a photomultiplier tube for amplifying the second beam.

12. The system according to claim 11, further including a compound parabolic collector coupled to the detector for collecting the second beam over an area greater than a working surface area of the photomultiplier tube.

13. The system according to claim 1, further including a third collector disposed towards a second surface of the laminate opposite the first surface and remote from the light source for collecting a third beam passing through the laminate and producing a respective third collector signal;
   said analyzing means being also coupled to the third collector and responsive to the third collector signal for analyzing defects in a hole in the laminate.

14. The system according to claim 13, wherein the third collector includes:
   an optical light guide formed of a fluorescent material and being shielded by a third filter for preventing passage therethrough of any fluorescence induced within the fluorescent material,
   a third planar reflecting surface at a first end of the optical light guide for reflecting light directed thereto back through the optical light guide towards a second end thereof remote from the first end, and
   a detector at the second end of the optical light guide for producing the third collector signal;
   whereby said third beam passes through the third filter towards the optical light guide and induces fluorescence in the fluorescent material of the optical light guide which fluorescence is internally reflected therein so as to be directed towards the detector while being blocked by the third filter so as to prevent it from escaping from the optical light guide.

15. The system according to claim 14, wherein the detector includes a photomultiplier tube for detecting the third beam.

16. The system according to claim 15, further including an integrating cylinder at the second end of the optical light guide for receiving the third beam on an internal reflecting surface thereof and for reflecting the third beam towards the detector.

17. The system according to claim 1, further including at least one fourth planar reflecting surface at a corresponding side of the collection optics for forming an image of the elliptical reflecting surface and thereby at least doubling an effective area thereof.

18. An optical inspection system for distinguishing between first and second components of a first surface of a laminate having said first component disposed on the second component, the system comprising:
   a collection optics including a cylindrical concave elliptical reflecting surface and having a first focal line coplanar with the first surface of the laminate,
   a light source in fixed spatial relationship with the collection optics for directing a beam of light through an aperture in the collection optics towards the laminate so as to strike the first surface along the first focal line and to produce from a first area of the first component a substantially conical fluorescent emission having a first apex angle and so as to be reflected by a second area of the second component as a substantially conical reflection beam having a second apex angle,
   a first filter disposed near a second focal line of the elliptical reflecting surface for intercepting the fluorescent emission and the reflection beam and for seeparating the fluorescent emission from the reflection beam,
   a first collector for collecting the separated fluorescent emission emanating from a limited area of said first area and producing a respective first collector signal,
   a pair of limit stops disposed near the second focal line for partially intercepting the reflected fluorescent emission so as thereby to limit the area within said first area from which fluorescent emission is collected by the first collector,
   a second collector for collecting the separated reflection beam emanating from a limited area of said second area and producing a respective second collector signal, and
   analyzing means coupled to the first and second collectors and responsive to the respective first and second collector signals for analyzing the first and second components of a laminate.

* * * * *